United States Patent [19]

Driskell

[11] 4,302,188
[45] Nov. 24, 1981

[54] PROSTHETIC DENTAL IMPLANTS

[75] Inventor: Thomas D. Driskell, Worthington, Ohio

[73] Assignee: Bio-Dynamics, Inc., Indianapolis, Ind.

[21] Appl. No.: 114,977

[22] Filed: Jan. 24, 1980

[51] Int. Cl.³ .............................................. A61C 8/00
[52] U.S. Cl. ..................................... 433/173; 433/176
[58] Field of Search ................................ 433/176, 173

[56] References Cited

U.S. PATENT DOCUMENTS

| | | | |
|---|---|---|---|
| 3,928,914 | 12/1975 | Kozlousky | 433/176 |
| 3,950,850 | 4/1976 | Driskell | 433/173 |
| 4,050,157 | 9/1977 | Fagan et al. | 433/176 |
| 4,231,120 | 11/1980 | Day | 433/173 |

Primary Examiner—R. Peshock
Attorney, Agent, or Firm—Woodard, Weikart, Emhardt & Naughton

[57] ABSTRACT

A prosthetic dental implant for anchoring to the mandible or maxilla for supporting artificial teeth and dentures includes a substantially flat yet slightly tapering endosteal blade portion constructed of a titanium alloy and including two columns of oblong slot-like apertures interior thereto and two edge columns of half-length oblong slot-like apertures. Support for an artificial tooth is provided by means of a support post which has a substantially circular lateral cross section throughout and an enlarged part-spherical lower portion and an upwardly and inwardly tapering portion thereabove. In an alternative arrangement, the vented concept provided by the slot-like apertures is replaced by a solid blade which includes a plurality of wedge-like lip portions outwardly extending from each side of the anchoring member and defining a recessed channel between adjacent lip portions, the lip portions and recessed channels on one side of the anchoring member being staggered from those on the opposite side.

15 Claims, 9 Drawing Figures

PROSTHETIC DENTAL IMPLANTS

BACKGROUND OF THE INVENTION

This invention relates in general to oral prosthetic implants and in particular to dental prosthetic implants which are surgically implantable and provide support means for crown replacements and artificial teeth.

In order to replace teeth which have been lost, whether by damage from an accident or injury or by disease, dentists and oral surgeons may utilize either a permanent or removable bridge. However, certain situations dictate somewhat more involved corrective measures, such as implanting a partial denture which is one form of prosthetic restoration. A partial denture may be a tooth-borne, tooth and mucosal-borne or mucosal-borne prosthesis, and the design and fit is critical to its suitability for the particular patient because of the relatively high force loads to be exerted upon such prosthetic devices. One of the primary disadvantages of partial dentures is the fact that the partial denture receives marginal load support from the underlying alveolar bone at the vacant tooth site or sites, thus forcing the transfer of abnormal lateral stresses to abutting teeth with destruction of peridontal tissues.

The following listed patents disclose apparata which have been associated with various attempts to implant relatively rigid structures into the mandible. While each may have provided some benefit or improvement to the particular area of technology at the time of their conception, the present invention disclosed herein provides still further benefits and improvements to each of these various prior art devices.

| Patent No. | Patentee |
| --- | --- |
| 3,577,853 | Roberts |
| 3,641,671 | Roberts |
| 3,777,402 | Roberts |
| 3,889,375 | Roberts |
| 3,739,476 | Roberts |
| 3,950,850 | Driskell et al. |
| 2,628,929 | German (Bandettini) |
| 3,729,825 | Linkow et al. |
| 3,881,251 | Valen |
| 4,050,157 | Fagan, Jr. et al. |
| 4,121,340 | Patrick |
| 3,797,113 | Brainin |
| 3,465,441 | Linkow |
| 4,024,639 | Weiss et al. |
| 3,851,393 | Weiss et al. |

Roberts (3,577,853) discloses an implant which is designed to be mounted specifically in the ramus or retromolar portion of the mandible or jawbone and includes an elongated main body carrying a post extending up from the forward end of the main body and passing up through the epithelium.

Roberts (3,641,671) discloses a permanent frame for removably supporting an artificial denture for the entire lower jaw. The frame comprises a rigid bar sized and shaped to correspond to the mandible and denture and the bar terminates at each end in a ramus implant and has an integral intraosseous blade at the central portion providing a holding implant in the front of the mandible.

Roberts (3,777,402) discloses a permanent frame for removably supporting an artificial denture in a molar area of the lower jaw when there is a sound natural bicuspid or cuspid tooth adjoining the area. The frame includes a rigid bar with the rear end formed into a ramus implant and the exposed portion of the bar is sized and shaped to conform to the molar area in question.

Roberts (3,889,375) discloses a frame portion for implanting into a correspondingly shaped upwardly extending channel cut longitudinally in the alveolar ridge of the upper jaw. The frame has a rear extension arranged to project through an aperture cut in the pterygoid bone and more particularly in an aperture cut just above the pyramidal process.

Roberts (3,739,476) discloses a denture support frame which includes a rigid bar which is sized and shaped to correspond to the alveolar ridge of the upper jaw. Each end of this main portion is turned approximately 90° to extend a short distance upwardly and is again turned approximately 90° so as to extend forwardly to form an implant which is driven anteriorly into the posterior tuberosity of the maxillary ridge.

Driskell discloses a prosthetic dental implant which is surgically plantable in the maxillary and mandibular alveolar bones. The implant includes a support base with a protruding post onto which one or more prosthetic crown replacements may be mounted. The implant is high-purity, high-density, low-porosity unitary alumina body and includes a serrated-shaped base.

The West German reference discloses a dental implant which is fitted into the jawbone and includes one portion which is inserted into the cancellous tissue beneath the jawbone compact tissue and includes at least one stump portion projecting from this part into the buccal cavity.

Linkow et al. discloses an oral implant of the vented blade type which includes a relatively thin vented blade portion adapted to be driven into a groove in the patient's jawbone and a crown supporting head and a neck portion connecting the crown supporting head to the blade portion.

Valen discloses a prefabricated tooth system which serves as a permenently secured tooth section which is easily removable for purposes of repair or modification. The tooth system comprises a bar which spans the space left by the missing teeth.

Fagen, Jr. et al. discloses a dental implant for anchoring attachments to the jawbone and includes a flat base embedded entirely within the bone tissue of the mandibular or maxillary ridge. A support head is connected to the base by a shank having a necked down portion spaced from the base and confined to the gingival.

Patrick discloses a combination bladevent subperiosteal implant in which the abutment post which bears an artificial tooth or a tooth in a full arch splint is isolated from and only indirectly attached to the bladevent body through a subperiosteal portion of the implant.

Brainin discloses a dental implant member formed of substantially nonporous, isotropic carbon having a textured and dentated lower portion. The implant member is provided with means for attaching an artificial crown section thereto.

Linkow discloses a device for implanting an artificial tooth and includes a blade with an opening therein and a free end defining a sharp edge. A support portion extends up from the blade to which support portion a force may be applied which is distributed over the blade so as to facilitate the implantation of the blade in the jawbone of the patient. Once the blade is implanted, the artificial tooth structure is secured to the support portion which extends up from the gum region.

Weiss et al. (4,024,639) discloses a dental implant which is embedded within a body of acrylic material in a channel formed in the jawbone such that no portion of the implant comes in contact with the bone. The implant includes one or more projecting pins for supporting an artificial tooth and a series of lateral projections which extend into the acrylic material to hold the implant in place.

Weiss et al. (3,851,393) discloses an oral implant of the vented blade type which includes a relatively thin vented blade adapted to be seated into the groove of the patient's jawbone, a crown supporting head and a neck integrally connecting the head to the blade. The blade has a curvature corresponding to the average curvature of a frontal jawbone segment and is inclined relative to the head so that the head remains relatively vertical while the blade follows the jutting angle of the frontal jawbone segment.

One feature required with each of the disclosed apparata is some type of anchoring or securing means for the prosthetic implant. This is typically accomplished by a stake or post having vents or alternatively a serrated or sawtooth contour. Slight variations in the design of such stakes, while appearing to be subtle, can have a significant effect as to the strength and rigidity of the implant. For example, a sawtooth or serrated contoured stake as disclosed by Linkow et al. is desired for ease of insertion but is unfortunately susceptible to migration deeper into the bone with those forces acting on the upper surface of the head. Consequently, it would be an improvement from the standpoint of strength to reverse the direction of the sawtooth so as to act against such forces and prevent deeper migration into the jawbone. The Driskell et al. patent incorporates such a concept but does not also utilize vents which are also beneficial in that they permit the bone to grow into and through the vents thereby locking the implant in place.

The present invention incorporates a variety of improvement features into a single prosthetic implant and the concepts disclosed are suitable as part of a ramus frame as well as an individual tooth replacement. While certain similarities may exist between the invention disclosed herein and various prior art references, the specific combinations described are novel and provide a number of advantages.

SUMMARY OF THE INVENTION

A prosthetic dental implant for anchoring to the mandible according to one embodiment of the present invention comprises a U-shaped frame member, a first ramus anchoring member longitudinally extending from one end of the U-shaped frame member, a second ramus anchoring member longitudinally extending from the other end of said U-shaped frame member and a centrally disposed anchoring member laterally depending from the base of said U-shaped frame member. Each of the anchoring members is constructed of metal and arranged into a blade-like shape wherein a plurality of lengthwise extending and a plurality of widthwise extending portions define a plurality of slot-like apertures.

A prosthetic dental implant arranged to provide a supporting post or posts for one or more artificial teeth according to another embodiment of the present invention comprises a substantially flat, blade-like anchoring member including a plurality of oblong slot-like apertures disposed therein and a support post joined to the uppermost edge of the anchoring member, the support post having a substantially lateral cross section throughout and the support post tapering inwardly as it extends upwardly from the enlarged lower portion.

A prosthetic dental implant arranged to provide a supporting post or posts for one or more artificial teeth according to yet another embodiment of the present invention comprises a blade-like anchoring member having a periphery shape which is substantially rectangular and including a plurality of longitudinally extending, wedge-shaped lip portions and a support post which is joined to the uppermost edge of the anchoring member. The lip portions are joined together as a continuous member wherein the outwardly protruding edges on one side of the anchoring member are substantially uniformly staggered between the outwardly protruding edges on the opposite side of the anchoring member.

One object of the present invention is to provide an improved prosthetic dental implant.

Related objects and advantages of the present invention will be apparent from the following description.

DESCRIPTION OF THE PREFERRED EMBODIMENTS

Figure 1:
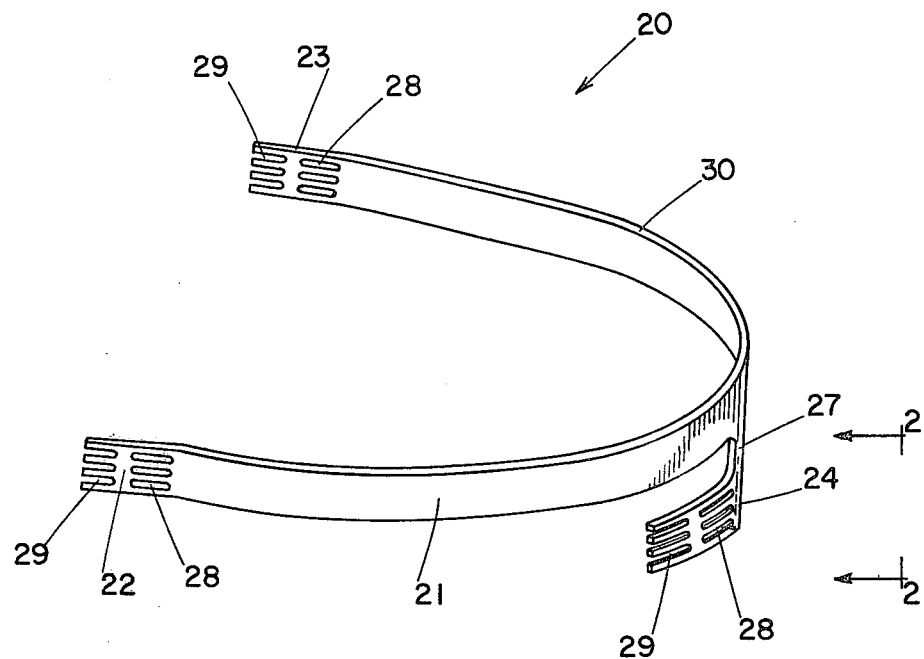
FIG. 1 is a perspective view of a ramus frame prosthetic dental implant according to a typical embodiment of the present invention.
Figure 2:
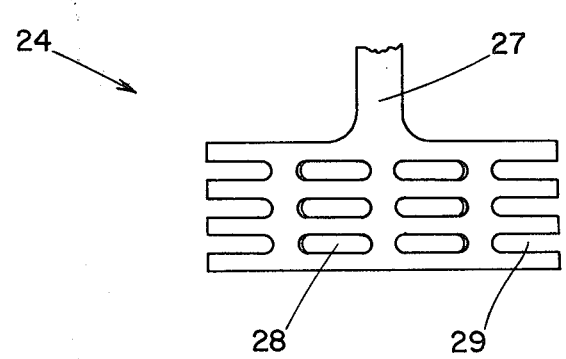
FIG. 2 is a partial, front elevation view of a centrally disposed anchoring member comprising a portion of the FIG. 1 prosthetic dental implant.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated prosthetic dental implant 20 which includes a U-shaped frame 21 which has a size and contour shape which corresponds to the mandible and three anchoring members 22, 23 and 24 which secure the U-shaped frame in place.

Anchoring members 22 and 23 are arranged with a relatively thin blade-like vented design and are suitably configured and sized for insertion into the ramus portion of the mandible at a location above the alveolar border. Therefore, these two anchoring members 22 and 23 are positioned with respect to the remainder of U-shaped frame 21 such that the frame curves downwardly as it extends forwardly in order to conform to the upper edge of the mandible. The third anchoring member 24 extends downwardly from the front portion of the U-shaped frame 21 and is joined thereto by neck stem 27. Although anchoring member 24 is similarly shaped in some regards to members 22 and 23 in that it is blade-like and vented, it does have a curved shape which conforms closely to the curvature of the front portion of the mandible into which it is inserted. These three anchoring members 22, 23 and 24 each constitute intraosseous blades and their vented aspect is provided by means of a plurality of oblong, slot-like apertures 28 and 29 extending therethrough. Once these anchoring members are implanted to their corresponding and surrounding bone portions, these apertures provide an anchoring means for the prosthetic dental implant in that they permit bone growth therethrough.

In order to simplify the implant procedure, it is desirable that anchoring members 22, 23 and 24 be constructed with a minimal thickness dimension such that their passage into the corresponding and surrounding bone portions is simplified. Of course, the offsetting consideration in making these endosteal blades thinner is that certain strength will be lost and conceivably subject these members to bending. One solution to this is to utilize a material such as a high-strength alloy wherein the thickness of the anchoring members can be significantly reduced without compromising strength and durability. One suitable material for prosthetic dental implant 20 is a titanium alloy such as a 6Al-4V ELI alloy which has an ASTM designation of F136-70. Such a material enables an endosteal blade thickness of between 0.020 and 0.040 inches without sacrificing the required strength. However, other related materials are also suitable and the subject invention is not limited to the use of titanium. A further concern with the use of a significantly thinner material is that the surface area contacted by the bone portions growing therethrough is less for the same size and number and venting apertures. One way to compensate for the reduced thickness of the blade portions is to increase the number and/or size of apertures and the present invention has achieved this result by including oblong slot-like apertures which occupy a majority (more than one-half) of the total surface area of the anchoring members rather than incorporating only a few circular apertures as is commonly done in various prior art devices. Although anchoring members 22, 23 and 24 incorporate a plurality of full oblong, slot-like apertures 28, the maximizing of the number of apertures requires including a plurality of partial oblong, slot-like apertures 29, in the exemplary embodiment half apertures 29 are incorporated on the outer edges of the various anchoring members.

While anchoring members 22, 23 and 24 may be substantially flat and of a uniform thickness throughout their entire surface, it is envisioned that the leading edge which must be first inserted into the particular corresponding bone portion be of a slightly thinner nature than the remainder and thus a general tapering shape is the result. Such a taper ranges from as low as 0.025 inches in thickness at the thinnest part up to as much as 0.062 inches or greater at the thickest portion. With the various anchoring members fully inserted and properly positioned within their corresponding and surrounding bone portions, the upper surface 30 of U-shaped frame member 21 is disposed in proper position and contour adjacent the upper portion of the mandible in order to accept and support an artificial denture for the entire lower jaw.

Figure 3:
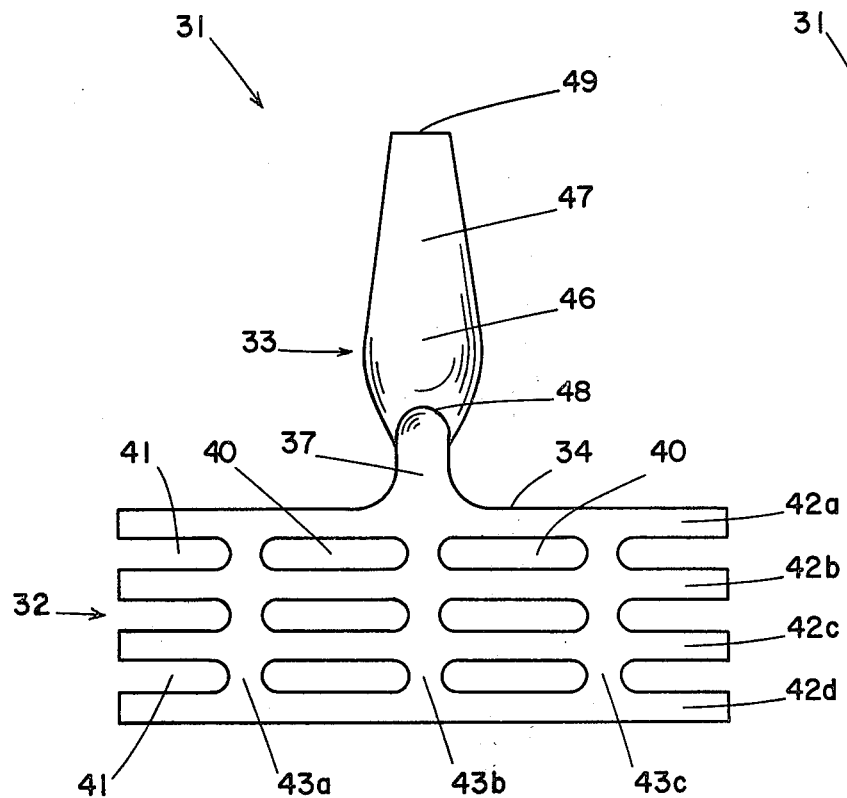
FIG. 3 is a front elevation view of a prosthetic dental implant according to a typical embodiment of the present invention.
Figure 4:
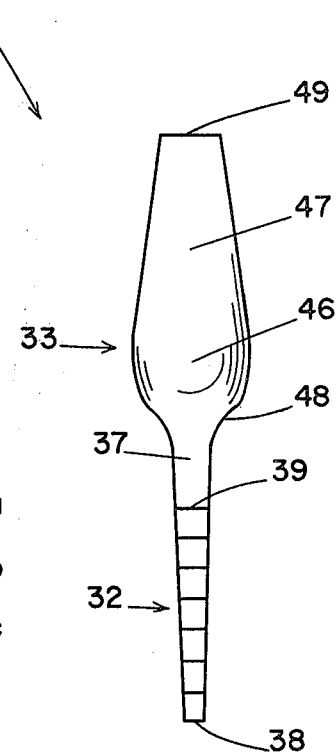
FIG. 4 is a side elevation view of the FIG. 3 prosthetic dental implant.

Referring to FIGS. 3 and 4, a prosthetic dental implant 31 is illustrated and includes a substantially flat, blade-like anchoring member 32 and a support post 33 joined to the upper most portion 34 of anchoring member 32 by neck portion 37. Anchoring member 32 is generally rectangular in periphery shape and has a slightly tapered thickness which ranges between the dimensions of 0.025 inches at lower end 38 and 0.062 inches at upper end 39. The taper of anchoring member 32 is substantially uniform throughout and both the front and back surfaces of anchoring member 32 are substantially flat throughout. Disposed within the surface of anchoring member 32 are a plurality of full oblong, slot-like apertures 40 and a plurality of half oblong, slot-like apertures 41. These various apertures are defined by a series of horizontally and longitudinally extending sections of material 42a, 42b, 42c and 42d in combination with vertically extending sections of material 43a, 43b and 43c.

Support post 33 includes a substantially part-spherical enlarged lower portion 46 and an inwardly tapering frustoconical upper portion 47. Support post 33 has a substantially circular lateral cross section throughout its entire length which is defined as that portion extending between neck portion interface line 48 and top surface 49. Support post 33 provides that portion of prosthetic dental implant 31 which receives the dental prosthesis.

Blade-like anchoring member 32 is configured similarly to anchoring members 22, 23 and 24 in that the plurality of both full oblong apertures and half oblong apertures 40 and 41, respectively, enable the surrounding bone portions to grow therethrough thus providing excellent anchoring for this particular implant. Prosthetic dental implant 31 is constructed of a high-strength alloy such as titanium (6Al-4V ELI Alloy) and thus the thickness of blade-like anchoring member 32 can be kept at a minimum without sacrificing the necessary strength and durability while still permitting forced insertion into the bone. With such a reduced thickness, it is important that the overall size of anchoring member 32 be sufficient for proper implanting and the length and width dimensions of this rectangular periphery are approximately 0.82 inches and 0.28 inches, respectively.

Figure 5:
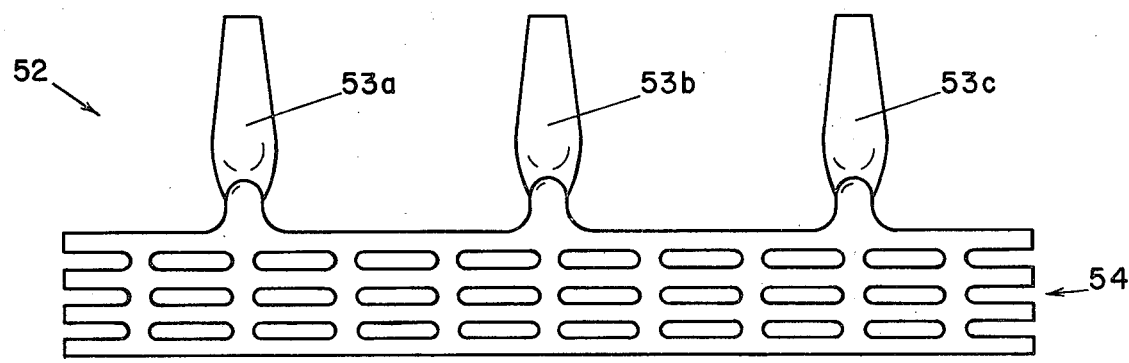
FIG. 5 is a front elevation view of an alternative prosthetic dental implant similar to the FIG. 3 prosthetic dental implant.

Referring to FIG. 5, an alternative to the FIG. 3 prosthetic dental implant 31 is illustrated. Prosthetic dental implant 52 includes a plurality of support posts 53a, 53b and 53c and a single integral blade-like anchoring member 54. In virtually all respects, prosthetic dental implant 52 is identical to prosthetic dental implant 31, the only difference being that dental implant 52 includes a plurality of support posts. It is to be understood that while dental implant 31 is disclosed for a single tooth replacement, it is envisioned that alternatives such as implant 52 are provided for when a plurality of teeth are to be replaced by artificial teeth and in which circumstances the teeth to be replaced are adjacent to one another.

Figure 6:
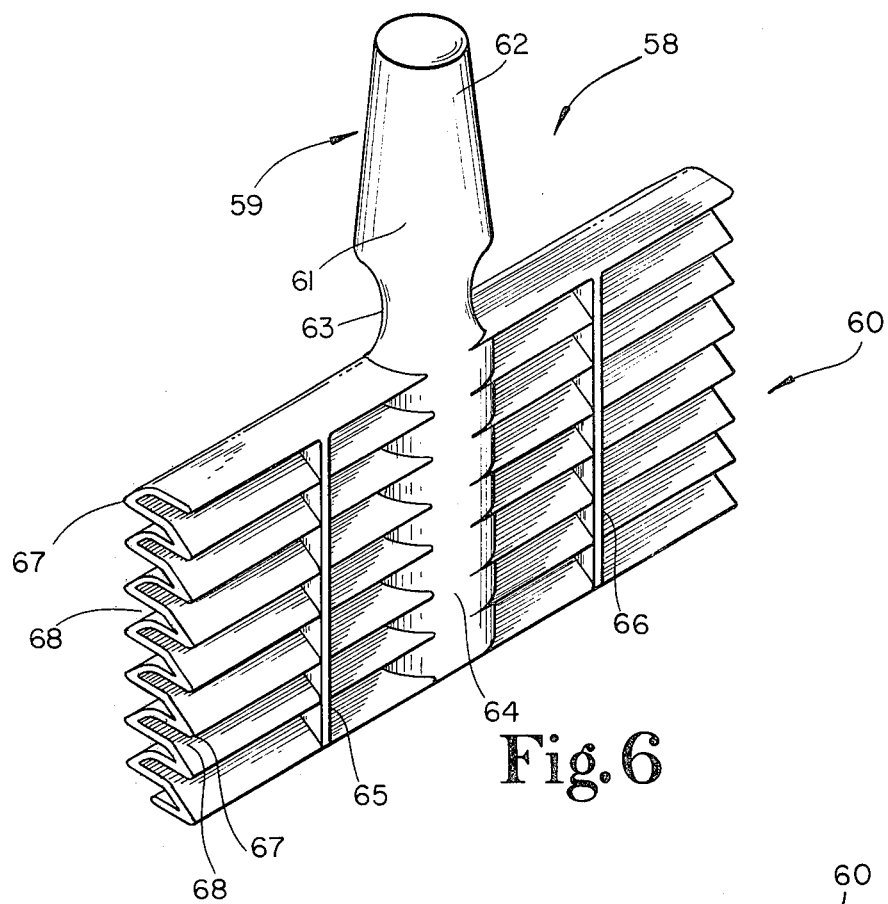
FIG. 6 is a perspective view of a prosthetic dental implant according to a typical embodiment of the present invention.

Referring to FIGS. 6 an 7, an alternative prosthetic dental implant embodiment is illustrated. Dental implant 58 includes a support post 59 and a blade-like anchoring member 60. Support post 59 includes an enlarged lower portion 61, an inwardly tapering upper portion 62 and a reduced diameter neck portion 63. Implant 58 represents a somewhat different anchoring concept than that represented by implant 31 and there are several structural differences between these two embodiments. One difference noted is that neck portion 63 extends downwardly into an enlarged cylindrical stem 64 which is concentric with the longitudinal axis of support post 59. Equally spaced on opposite sides of stem 64 are divider bars 65 and 66 which segment blade-like anchoring member 60 into four somewhat evenly sized sections. The divider bars provide structural rigidity and stiffening to anchoring member 60. Each section includes a plurality of corrugations which include wedge-like lip portions 67 and recessed channels 68 disposed between adjacent lip portions. The lip portions of each of the four sections are aligned with each other such as to provide the appearance of continuous length with the exception of the segmenting effect provided by stem 64 and divider bars 65 and 66.

Figure 7:
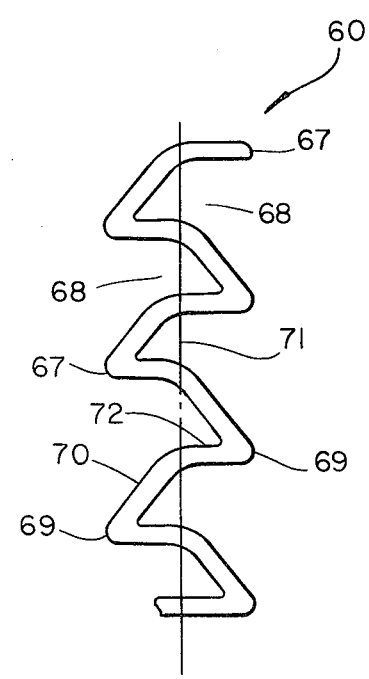
FIG. 7 is a diagrammatic side elevation view of the anchoring member portion of the FIG. 6 prosthetic dental implant.

The details of the geometry of wedge-like lip portions 67 in combination with recessed channels 68 is best illustrated by the diagrammatic representation of by FIG. 7 wherein it is seen that the lip portions 67 and recessed channels 68 on one side of anchoring member 60 are staggered from corresponding lip portions and recessed channels on the opposite side of anchoring member 60. In this manner, there is a continuous zig zag or sawtooth-type appearance to anchoring member 60 and the recessed channels provide a void in which the bone may grow to serve as a securing and anchoring means for the implant. Lip portions 67 are fabricated from substantially uniform thickness material throughout the four sections for the full height of anchoring member 60.

Figure 8:
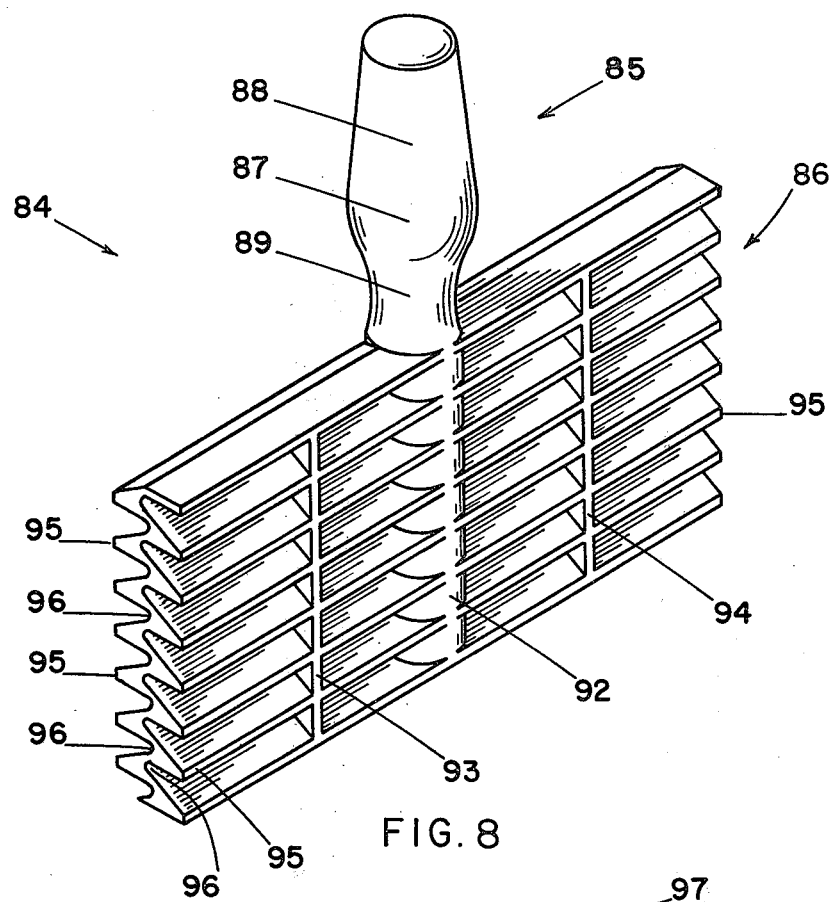
FIG. 8 is a perspective view of a prosthetic dental implant according to a typical embodiment of the present invention.
Figure 9:
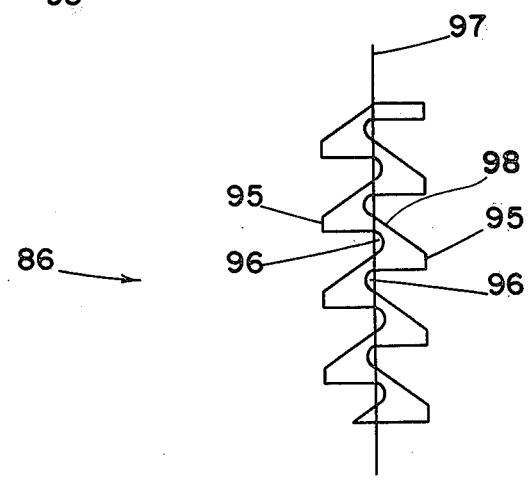
FIG. 9 is a diagrammatic side elevation view of the anchoring member portion of the FIG. 8 prosthetic dental implant.

The corrugations of implant 58 are configured with a series of segments. Extending upwardly from the point 69 of each lip portion is an inclined segment 70 disposed at approximately 45 degrees. This segment terminates near centerline 71 at which point segment 72 begins and extends substantially horizontal into point 69 of the adjacent, oppositely-facing lip portion. While this configuration is preferred, it is also envisioned that the segments can be blended into a single, constant curvature segment extending from one point to the adjacent, oppositely-facing point. Referring to FIGS. 8 and 9, a still further prosthetic dental implant design is illustrated. Prosthetic dental implant 84 includes a support post 85 and a blade-like anchoring member 86. Support post 85 includes an enlarged lower portion 87, an inwardly tapering upper portion 88 and a reduced diameter neck portion 89. Neck portion 89 of member 86 extends downwardly into an enlarged cylindrical stem 92 which is concentric with the longitudinal axis of support post 85. Equally spaced on opposite sides of stem 92 are divider bars 93 and 94 which segment blade-like anchoring member 86 into four somewhat evenly sized sections. Divider bars 93 and 94 serve to enhance the structural rigidity of anchoring member 86. Each section includes a plurality of corrugations which include wedge-like lip portions 95 and recessed channels 96 disposed between adjacent lip portions. The lip portions of each of the four sections are aligned with each other such as to provide the appearance of continuous length with the exception of the segmenting effect provided by stem 92 and divider bars 93 and 94.

The details of the geometry of wedge-like lip portions 95 in combination with recessed channels 96 is best illustrated by the diagrammatic representation of FIG. 9 wherein it is seen that the lip portions 95 and recessed channels 96 on one side of anchoring member 86 are staggered from corresponding lip portions and recessed channels on the opposite side of anchoring member 86. In this manner, there is a continuous zig zag or sawtooth-type appearance to anchoring member 86 and the recessed channels provide the same type of void in which the bone may grow to serve as a securing and anchoring means for the implant. One distinction between anchoring member 86 and anchoring member 60 is that the material thickness of the lip portions 95 is not substantially uniform throughout and there is a noticeable variation between the centerline area and outer edges. Each pair of adjacent oppositely-facing lip portions are joined together by a connecting segment 98 which has a thinner cross section than the lip portions. Due to the wedge-shaped appearance of recessed channels 96, the interior depth, similar to that of implant 58, provides additional surface area for each of the recessed channels and this enables greater anchoring member surface-area-to-bone contact and improves the anchoring and locking feature once bone growth begins into these channels.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A prosthetic dental implant arranged to provide a supporting post for one or more artificial teeth, said prosthetic dental implant comprising:
    a blade-like insertion member for anchoring into bone tissue, said insertion member including a plurality of oblong slot-like apertures disposed therein and a plurality of partial oblong slit-like apertures extending inwardly from the edges of said insertion member; and
    a support post joined to the uppermost edge of said insertion member, said support post having a substantially circular lateral cross section throughout and an enlarged lower portion and said support post tapers inwardly as it extends upwardly from said enlarged lower portion.

2. The prosthetic dental implant of claim 1 wherein said blade-like insertion member has a generally rectangular solid shape and the width and length dimensions of said shape are each at least five times the maximum thickness dimension of said insertion member.

3. The prosthetic dental implant of claim 2 in which said implant is constructed of titanium.

4. The prosthetic dental implant of claim 1 which further includes a neck portion having a reduced diameter from that of the enlarged lower portion of said support post and connecting said support post to the upper edge of said insertion member.

5. The prosthetic dental implant of claim 1 which further includes a plurality of support posts joined to the uppermost edge of said insertion member in a spaced-apart relationship to each other.

6. A prosthetic dental implant arranged to provide a supporting post for one or more artificial teeth, said prosthetic dental implant comprising:
- a blade-like anchoring member having a periphery shape which is substantially rectangular and including a plurality of longitudinally extending corrugations, said corrugations being joined together as a continuous member and including outwardly protruding edge portions on each side of said anchoring member, edge portions on one side of said anchoring member being staggered between edge portions on the opposite side; and
- a support post joined to the uppermost edge of said anchoring member.

7. The prosthetic dental implant of claim 6 wherein said corrugations are configured into oppositely-facing wedge-shaped lip portions, adjacent lip portions on the same side of said anchoring member defining a recessed channel therebetween.

8. The prosthetic dental implant of claim 6 wherein said support post has a substantially circular lateral cross section throughout and an enlarged part-spherical lower portion.

9. The prosthetic dental implant of claim 6 wherein said corrugations are configured into staggered, oppositely-facing lip portions, said lip portions on each side of said anchoring member defining a recessed channel therebetween, the interior depth of said channels extending beyond the thickness centerline of said anchoring member.

10. The prosthetic dental implant of claim 6 wherein said implant is constructed of a titanium alloy.

11. The prosthetic dental implant of claim 7 wherein said corrugations have a substantially uniform thickness throughout.

12. The prosthetic dental implant of claim 11 wherein each lip portion includes an inclined segment and a horizontal segment.

13. The prosthetic dental implant of claim 7 wherein said adjacent, oppositely-facing lip portions are joined by a connecting segment and the thickness of said lip portions is greater than the thickness of said connecting segments.

14. A prosthetic dental implant arranged to provide a supporting post for one or more artificial teeth, said prosthetic dental implant comprising:
- a substantially flat blade-like anchoring member including a plurality of oblong slot-like apertures disposed therein, said anchoring member further includes a plurality of side edge apertures opening outwardly and a plurality of oblong slot-like apertures arranged into two interior columns, said side edge apertures also arranged into two columns; and
- a support post joined to the uppermost edge of said anchoring member, said support post having a substantially circular lateral cross section throughout and an enlarged lower portion and said support post tapers inwardly as it extends upwardly from said enlarged lower portion.

15. A prosthetic dental implant arranged to provide a supporting post for one or more artificial teeth, said prosthetic dental implant comprising:
- a substantially flat blade-like anchoring member including a plurality of oblong slot-like apertures disposed therein;
- a support post joined to the uppermost edge of said anchoring member, said support post having a substantially circular lateral cross section throughout and an enlarged lower portion and said support post tapers inwardly as it extends upwardly from said enlarged lower portion; and
- a neck portion having a reduced diameter from that of the enlarged lower portion of said support post and connecting said support post to the upper edge of said anchoring member, said anchoring member including six full-length oblong slot-like apertures and six half-length oblong slot-like apertures.

* * * * *